(12) United States Patent
Arai et al.

(10) Patent No.: US 7,022,878 B2
(45) Date of Patent: Apr. 4, 2006

(54) ORGANIC BORATE COMPOUNDS AND THE NONAQUEOUS ELECTROLYTES AND LITHIUM SECONDARY BATTERIES USING THE COMPOUNDS

(75) Inventors: Juichi Arai, Tokyo (JP); Hideaki Katayama, Tokyo (JP); Mitsuru Kobayashi, Tokyo (JP); Hiroyuki Yamaguchi, Saitama (JP); Hideki Takahashi, Saitama (JP); Masaru Kato, Saitama (JP)

(73) Assignees: Hitachi, Ltd., Tokyo (JP); Kanto Kagaku Kabushiki Kaisha, Tokyo (JP)

( * ) Notice: Subject to any disclaimer, the term of this patent is extended or adjusted under 35 U.S.C. 154(b) by 0 days.

(21) Appl. No.: 10/972,404

(22) Filed: Oct. 26, 2004

(65) Prior Publication Data

US 2005/0171383 A1 Aug. 4, 2005

Related U.S. Application Data

(60) Division of application No. 10/641,085, filed on Aug. 15, 2003, now Pat. No. 6,824,928, which is a continuation of application No. 09/957,455, filed on Sep. 21, 2001.

(30) Foreign Application Priority Data

Sep. 21, 2000 (JP) ............................. 2000-291968

(51) Int. Cl.
*C07F 5/02* (2006.01)
(52) U.S. Cl. ..................................................... 562/882
(58) Field of Classification Search ................. 562/882
See application file for complete search history.

(56) References Cited

U.S. PATENT DOCUMENTS

| 5,055,974 | A | | 10/1991 | Washio et al. |
| 5,660,947 | A | * | 8/1997 | Wuhr ......................... 429/199 |
| 6,548,212 | B1 | | 4/2003 | Heider et al. |

FOREIGN PATENT DOCUMENTS

| DE | 43 16 104 | | 5/1993 |
| EP | 1 035 612 A1 | | 9/2000 |
| JP | 5-326018 | | 12/1993 |
| JP | 06-215775 | | 8/1994 |
| JP | 7-65843 | | 3/1995 |
| JP | 08-196911 | | 8/1996 |
| JP | 9-97627 | | 4/1997 |
| JP | 10-12272 | | 1/1998 |
| JP | 10-265479 | | 10/1998 |
| JP | 11-30713 | | 11/1999 |
| JP | 11-329497 | | 11/1999 |
| JP | 2000-268863 | | 9/2000 |
| JP | 2000-516930 | | 12/2000 |
| JP | 2001-85058 | | 3/2001 |
| JP | 2001-181282 | * | 7/2001 |
| WO | WO 94/27335 | | 11/1994 |
| WO | WO 98/28807 | | 7/1998 |

OTHER PUBLICATIONS

A Collection of Preprints, the 40th Forum on Batteries, pp. 453-454 (1999) Application to Lithium Battery Electrolyte of the Chelate Type Lithium Salt with Salicylic Ligand (II).
A Collection of Preprints, the 40th Forum on Batteries, pp. 459-460 (1999) "Safety and Reliability of Lithium Ion Secondary Batteries Applied with Nonflammable Solvent Electrolyte".
M. Harriss et al., "The Trifluoroacetic Acid Solvent System, Part IV, Triple Ions" *Canadian Journal of Chemistry* (1972), 50(23), pp. 3789-3798.
Korean Office Action.
European Search Report.

* cited by examiner

*Primary Examiner*—Laura Weiner
(74) *Attorney, Agent, or Firm*—Crowell & Moring LLP

(57) ABSTRACT

Organic borates having the formula:

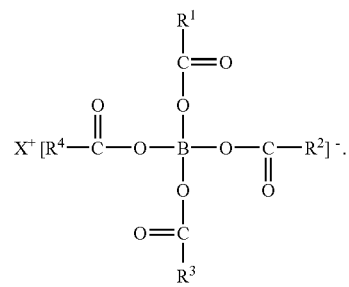

The borates are highly soluble in solvent of low dielectric constant. Also disclosed are nonaqueous electrolytes made from these organic borates; lithium secondary batteries with improved high-temperature storage characteristics; and electric appliances that comprises the battery and are free of protection circuits.

2 Claims, 8 Drawing Sheets

ORGANIC BORATE COMPOUNDS AND THE NONAQUEOUS ELECTROLYTES AND LITHIUM SECONDARY BATTERIES USING THE COMPOUNDS

BACKGROUND OF THE INVENTION

1. Field of the Invention

The present invention relates to a new organic borate compound, a nonaqueous electrolyte using the compound, and a lithium secondary battery and an electric appliance both using the electrolyte; the invention relating especially to a new organic borate compound high in oxidation resistance, a nonaqueous electrolyte improved in oxidation resistance by use of the compound, a lithium secondary battery and an electric appliance, both improved in cycle life by use of the electrolyte, and various applications of the electric appliance.

2. Description of the Prior Art

Lithium secondary batteries each made up of positive and negative electrodes capable of occluding and releasing lithium, a nonaqueous electrolyte, and other components, are high in energy density per weight and volume and in voltage. They are therefore hoped to be used as portable compact power supplies or as power supplies for electric automobiles. Since lithium secondary batteries have a high driving voltage of 3 V or more, they use a nonaqueous electrolyte wide in withstand voltage range. Compared with aqueous electrolytes, nonaqueous electrolytes have the drawbacks that they are low in electroconductivity and that a large portion of organic solvents suitable for an nonaqueous electrolyte are high in flammability (or low in flashing point).

For these reasons, researches for improving electroconductivity and, hence, the load characteristics of the battery, and researches for using a noncombustible or low-flammability organic solvent as the nonaqueous electrolyte for the battery, are taking place actively. An example of the former researches is reported in "A Collection of Preprints, the 40th Forum on Batteries, pp. 453~454, (1999)", and an example of the latter researches is reported in "A Collection of Preprints, the 40th Forum on Batteries, pp. 459~460 (1999)." To improve the electroconductivity of a battery, it is necessary either to improve the dissociation characteristics of the supporting electrolyte to be used for the battery, or to select an organic solvent enabling the dissociation characteristics of the supporting electrolyte to be improved. For the electrolyte, organic lithium salt is proposed as lithium salt excellent in dissociation characteristics over the lithium hexafluorophosphate ($LiPF_6$) or lithium tetrafluoroborate ($LiBF_4$) that is now mainly used. Above all, the lithium bis-(trifluoromethanesulfonyl)imide (LiN [$SO_2CF_3$]$_2$) shown in Japanese Application Patent Laid-Open Publication No. Hei 05-326018 is known as a promising material having high solubility against a nonaqueous electrolytic solvent in comparison to an inorganic electrolyte. It is indicated, however, that the lithium bis-(trifluoromethanesulfonyl)imide (LiN [$SO_2CF_3$]$_2$) has the drawback that it corrodes the aluminum used as the positive-electrode current collector for a secondary battery.

Also, organic lithium salt having boron to form its central ion and disalicylate to form its ligands, and organic lithium salt having boron to form its central ion and a benzenediolate derivative to form its ligands, are disclosed in Japanese Application Patent Laid-Open Publication No. Hei 07-65843. However, since these compounds have a benzene ring and are thus low in solubility, they cannot satisfy the electroconductivity or oxidation resistance required.

As disclosed in Japanese Application Patent Laid-Open Publication Nos. Hei 09-97627 and Hei 10-12272, to obtain noncombustibility or to ensure flameproofing, it is valid to use a fluorinated solvent. However, since the fluorine in fluorinated solvents is high in electron withdrawing ability, these solvents pose the problem that they deteriorate the electron releasing characteristics of their functional groups and, hence, the solubility and dissociation characteristics of lithium salt. Organic lithium salt has higher solubility than inorganic lithium salt, and is therefore a valid material.

For these reasons, the improvement of organic lithium salt is strongly desired as a promising material for improving the safety and performance of lithium secondary batteries.

SUMMARY OF THE INVENTION

The present invention is intended to supply: an organic borate compound from which a nonaqueous electrolyte high in electroconductivity can be created, and whose characteristics do not deteriorate even in a nonaqueous electrolyte having a noncombustible fluorinated solvent mixture; a lithium secondary battery using the organic borate compound; a nonaqueous electrolyte enabling the characteristics of an electrochemical capacitor to be improved; a long-life lithium secondary battery and an electric appliance, both using the nonaqueous electrolyte, and; various applications of the electric appliance.

Electroconductivity is determined by the number of lithium ions and the mobility level thereof. Also, solubility is considered to exist within the radius of the ions surrounded by the solvent. For these reasons, the present inventors have considered it possible to suppress local coagulation of the solvent by increasing the anion of lithium salt dimensionally and delocalizing the electric charge of the ions, and to obtain highly dissociative and highly soluble lithium salt by introducing into the anion a functional group which can improve the affinity between the anion and the solvent and increase the electron withdrawing ability of the central element in the anion. Consequently, the inventors have energetically studied such a compound to complete the present invention.

That is to say, the present invention relates to an organic borate compound characterized in that it is represented by general formula (1)

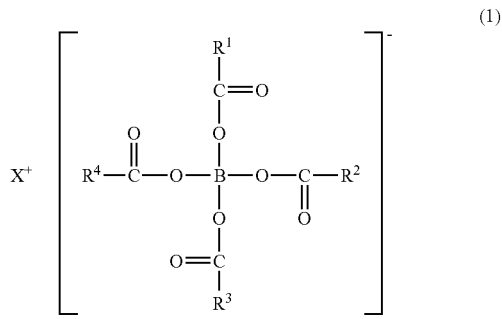

(1)

where X denotes lithium or quaternary ammonium or quaternary phosphonium and $R^1$, $R^2$, $R^3$, and $R^4$ each denote an independent halogen-atom displacement alkyl group whose carbon number ranges from 1 to 4.

The organic borate represented by general formula (1) above is a new compound excellent in solubility against a nonaqueous solvent, and the electrolytes using this compound are high in electroconductivity. More specifically, a halogen displacement acyloxy group having an excellent electron withdrawing ability and enabling an electric charge to be delocalized in a carbonyl group has been introduced into boron, the central element of the anion. Also, the ion radius of the anion has been increased and the electric charge of the ions has been delocalized. Consequently, it has been possible to improve solubility. For this reason, a nonflammable fluorinated solvent small in dipole moment and low in dielectric constant can also be applied to an electrolyte having such a supporting electrolytic property. Unlike imide-based organic salt, the compound described above does not corrode the current collector of aluminum, because the central ion of the compound is surrounded by ligands.

The organic borate compound in an embodiment of the present invention has the chemical structure represented as general formula 1, wherein X denotes lithium or quaternary ammonium quaternary phosphonium and $R^1$, $R^2$, $R^3$, and $R^4$ each denote an independent halogen-atom displacement alkyl group whose carbon number ranges from 1 to 4. In terms of molecular weight and oxidation stability, it is preferable that $R^1$, $R^2$, $R^3$, and $R^4$ are each a trifluoromethyl group or a pentafluoroethyl group.

A nonaqueous electrolyte that is very high in solubility against ring carbonate such as ethylene carbonate or propylene carbonate, against chain carbonate such as dimethyl carbonate or ethyl methyl carbonate, or against ether such as dimethoxyethane, and using each such solvent independently or in mixed form, can be obtained from the organic borate compound formed according to the present invention. In addition, a nonaqueous electrolyte high in electroconductivity can be obtained from either a compound using the fluorinated alkyl groups represented as $R^1$, $R^2$, $R^3$, and $R^4$ in general formula (1), or a compound using partially fluorinated alkyl groups, since these compounds have a solubility of at least 1.8 mol.dm$^{-3}$, even for a solution in which, in addition to the above-mentioned nonaqueous solvents, a nonflammable fluorinated solvent low in dielectric constant such as nonafluorobutyl methyl ether (tradename: HFE7100), is contained in the range from 5 to 90 volume percent. Furthermore, in addition to being wide in operating electric potential range because of its oxidation decomposition potential being high (about 5 V) against a lithium metal, the electrolyte obtained by dissolving such organic lithium borate does not corrode aluminum.

Examples of a compound which can be embodied using the organic borate pertaining to the present invention include: lithium tetrakis (trifluoroacetate) borate, lithium tetrakis (difluoroacetate) borate, lithium tetrakis (fluoroacetate) borate, lithium tetrakis (chlorodifluoroacetate) borate, lithium tetrakis (trichloroacetate) borate, lithium tetrakis (dichloroacetate) borate, lithium tetrakis (pentafluoropropanoate) borate, lithium tetrakis (3-chlorotetrafluoropropanoate) borate, lithium tetrakis (heptafluorobutanoate) borate, lithium tetrakis (2,2-bis-trifluoromethylbutanoate) borate, tetraethyl ammonium tetrakis (trifluoroacetate) borate, lithium tetrakis (difluoroacetate) borate, tetraethyl ammonium tetrakis (fluoroacetate) borate, tetraethyl ammonium tetrakis (chlorodifluoroacetate) borate, tetraethyl ammonium tetrakis (trichloroacetate) borate, tetraethyl ammonium tetrakis (pentafluoropropanoate) borate, tetraethyl ammonium tetrakis (3-chlorotetrafluoropropanoate) borate, tetraethyl ammonium tetrakis (heptafluorobutanoate) borate, tetraethyl ammonium tetrakis (2,2-bis-trifluoromethylbutanoate) borate, triethyl methyl ammonium tetrakis (trifluoroacetate) borate, tetraethyl phosphoniium tetrakis (trifluoroacetate) borate, triethl methyl phosphonium tetrakis (trifluoroacetate) borate etc.

Organic lithium borate based on the present invention can be synthesized using such a process as represented by, for example, the following formula:

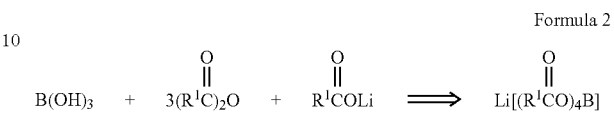

Formula 2

$$B(OH)_3 + 3(R^1C)_2O + R^1COLi \Longrightarrow Li[(R^1CO)_4B]$$

That is to say, organic lithium borate based on the present invention can be easily synthesized by generating reactions between boric acid, 3-quivalent acid anhydride, and lithium carbonate. However, the aforementioned process is one example of synthesizing the organic lithium borate pertaining to the present invention, and the synthesizing process is not limited to the aforementioned process. Also, organic borate ammonium salt or organic borate phosphonium salt can be obtained by using carboxylic acid quaternary ammonium salt or carboxylic acid quaternary phosphonium salt, instead of lithium carbonate.

A chain carbonate such as dimethyl carbonate, ethylmethyl carbonate, diethyl carbonate, dipropyl carbonate, or methylpropyl carbonate, a ring carbonate such as ethylene carbonate, propylene carbonate, butylene carbonate, triphloropropylene carbonate, or chloroethylene carbonate, vinylene carbonate, or dimethylvinylene carbonate, ring ester such as γ-butyrolactone or valerolactone, or chain ether such as 1,3-dioxysolan or tetrahydrofuran, can be used alone or in mixed form as the solvent for a nonaqueous electrolyte.

In addition to being used as the main supporting salt for a nonaqueous electrolyte, tetrahaloacetate borate based on the invention can be used as an additive, with $LiPF_6$, $LiBF_4$, $LiN(SO_2CF_2CF_3)_2$, $LiN(SO_2CF_3)_2$, or the like, as the main supporting salt.

The positive electrode of the lithium secondary battery can use a lithium composite oxide containing a transition element capable of occluding and releasing lithium, such as cobalt, nickel, or manganese. The negative electrode can use a lithium metal capable of occluding and releasing lithium, graphite, an amorphous carbon material, silica, an oxide of tin, or a complex consisting of these substances and carbon.

The separator of the lithium secondary battery can use polyethylene, polypropylene, or a microstructured porous film laminate consisting of these substances.

As described in detail above, using tetravalent boron as the central element of the anion in organic lithium borate based on the present invention, and adjusting the electron withdrawing ability and molecular size of the functional group to be bonded to the boron improves solubility against a solvent small in dipole moment and low in dielectric constant, such as a nonflammable fluorinated solvent, and thus enables the improvement of the electroconductivity of this solution and the provision of a nonaqueous electrolyte valid for lithium secondary batteries and electrochemical capacitors. Also, problems associated with the prior organic lithium salts, namely, the corrosion of aluminum and the insufficiency in oxidation suppression potential, can be solved by using the above-mentioned organic lithium borate as a supporting electrolyte. In addition, since oxidation resistance improves, the high-temperature storage characteristics of lithium secondary batteries can be improved.

Since organic lithium borates based on the present invention can be dissolved to concentrations of at least 0.8 mol/dm$^{-3}$ in solvent mixtures heavily laden with a fluorinated solvent, in particular, it is possible to obtain nonaqueous electrolytes that offer a maximum electroconductivity value at a low concentration of 0.4 mol/dm$^{-3}$.

Furthermore, according to the present invention, lithium secondary batteries from consumer product-use ones to large-capacity ones intended for electric power storage and for electric automobile use can be essentially made non-flammable and thus the appropriate lithium secondary battery significantly improved in safety and high in reliability can be supplied according to a particular application. In addition, improvement in the safety of conventional lithium secondary batteries and reduction in the weight and size thereof are anticipated.

Besides, it is possible to attain the significant effect that a battery with internal or external protection circuits reduced in weight and size or without these circuits can be constructed. Also, since the noncombustibility of electrolytes based on the present invention alleviates quantitative restriction of the electrolytes which can be stored at their manufacturing site, greater quantities of electrolytes than at present can be stocked for manufacturing use and there is the merit that this effect will lead to more appropriate adjustment of manufacture and stock.

DESCRIPTION OF THE PREFERRED EMBODIMENTS

Embodiments of the present invention are described in detail below. These embodiments, however, do not limit the invention.

(Embodiment 1)

The Synthesis and Identification of Lithium Tetrakis (Trifluoroacetate) Borate (Hereinafter Referred to as LB1)

Figure 1:
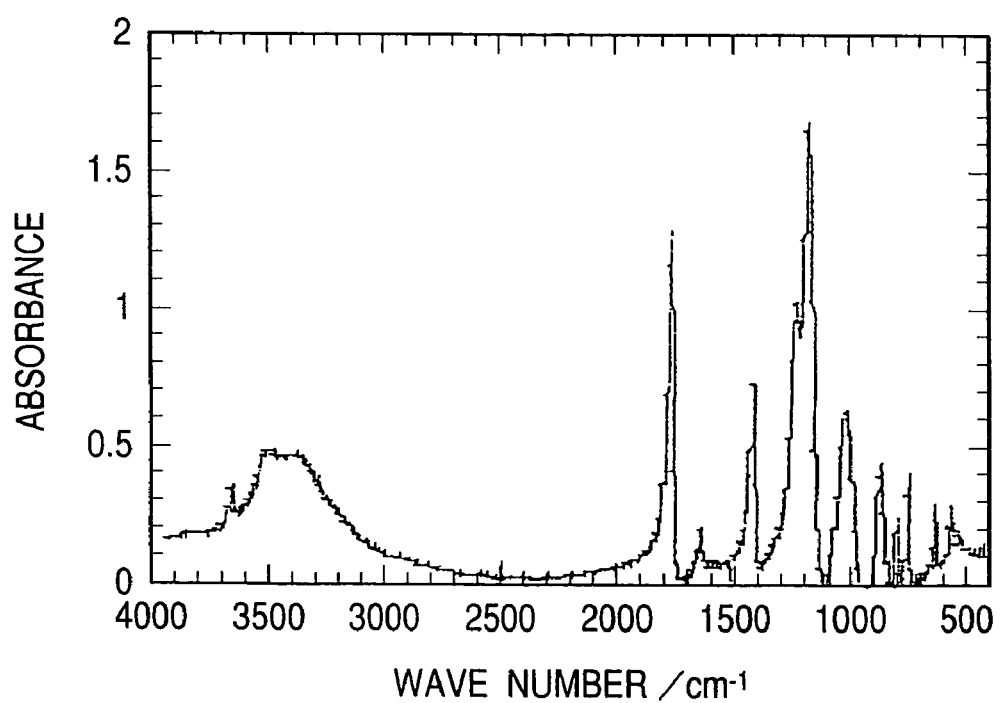
FIG. 1 is an infrared absorption spectral diagram showing an embodiment of the present invention.

After 4.9 g of boric acid, 9.5 g of lithium trifluoroacetate, and 100 ml of dimethyl carbonate were put into a 300-ml three-neck flask, 50 g of trifluoroacetate anhydride has been added dripwise while the entire mixture was being stirred under an ice-cooled status. After the dripping operation, the mixture has been stirred for about seven more hours at 80 degrees C. Next, the solvent has been removed from the reaction agent and the thus-obtained solid has been recrystallized using tetrahydrofuran. The thus-obtained crystal has been vacuum-dried to obtain LB1 at a yield of 67%. An infrared absorption spectral diagram of the compound which has thus been obtained is shown as FIG. 1.

Infrared absorption: 1,770 cm$^{-1}$ (C=O), 1,230 cm$^{-1}$ (C—F), 1,180 cm$^{-1}$ (C—F), 1,040 cm$^{-1}$ (C—O).

$^{11}$B-NMR spectrum (on a CD$_3$OD/trimethyl borate basis): δ-18.3 ppm. Ultimate analyses (Theoretical values in parentheses): Li=1.5(1.5)%, B=2.2(2.3)%, C=20.5(20.4)%. Melting point: 163° C. (decomposition).

(Embodiment 2)

The Synthesis and Identification of Lithium Tetrakis (Pentafluoropropanoate) Borate (Hereinafter Referred to as LB2)

Figure 2:
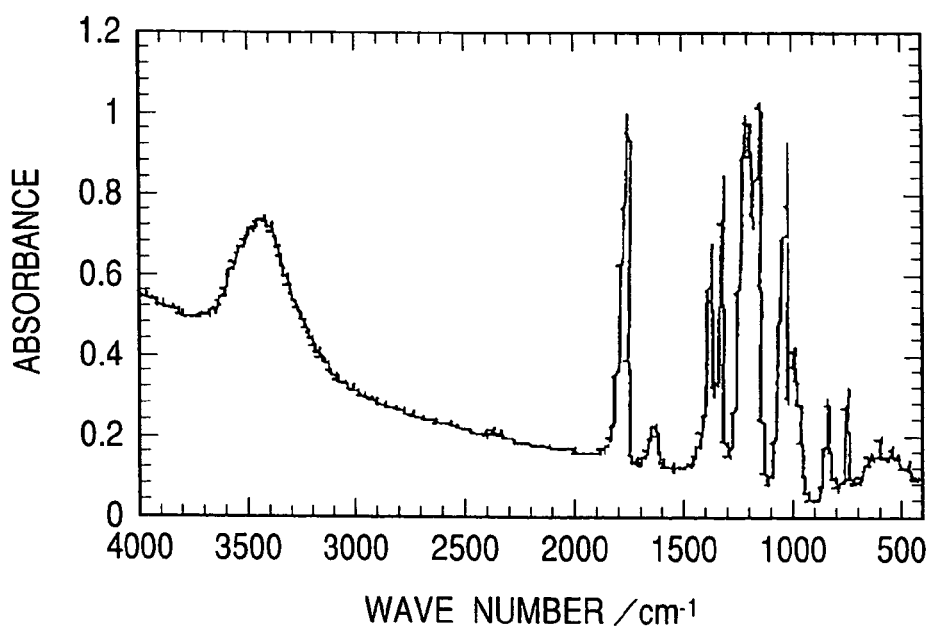
FIG. 2 is an infrared absorption spectral diagram showing another embodiment of the present invention.

After 8.8 g of boric acid, 24.2 g of lithium pentafluoropropionate, and 265 ml of dimethyl carbonate were put into a 1000-ml three-neck flask, 132.2 g of pentafluoropropionate anhydride has been added dripwise while the entire mixture was being stirred under an ice-cooled status. After the dripping operation, the mixture has been stirred for about 17 more hours at 90 degrees C. Next, the solvent has been removed from the reaction agent and the thus-obtained solid has been recrystallized using tetrahydrofuran. The thus-obtained crystal has been vacuum-dried to obtain LB2 at a yield of 38%. An infrared absorption spectral diagram of the compound which has thus been obtained is shown as FIG. 2.

Infrared absorption: 1,770 cm$^{-1}$ (C=O), 1,230 cm$^{-1}$ (C—F), 1,180 cm$^{-1}$ (C—F), 1,040 cm$^{-1}$ (C—O).

11B-NMR spectrum (on a CD$_3$OD/trimethyl borate basis): δ-18.6 ppm. Ultimate analyses (Theoretical values in parentheses): Li=1.0(1.0)%, B=1.3(1.6)%, C=21.8(21.5)%. Melting point: 198° C. (decomposition).

(Embodiment 3)

The Synthesis and Identification of Lithium Tetrakis (Trichloroacetate) Borate (Hereinafter Referred to as LB3)

Figure 3:
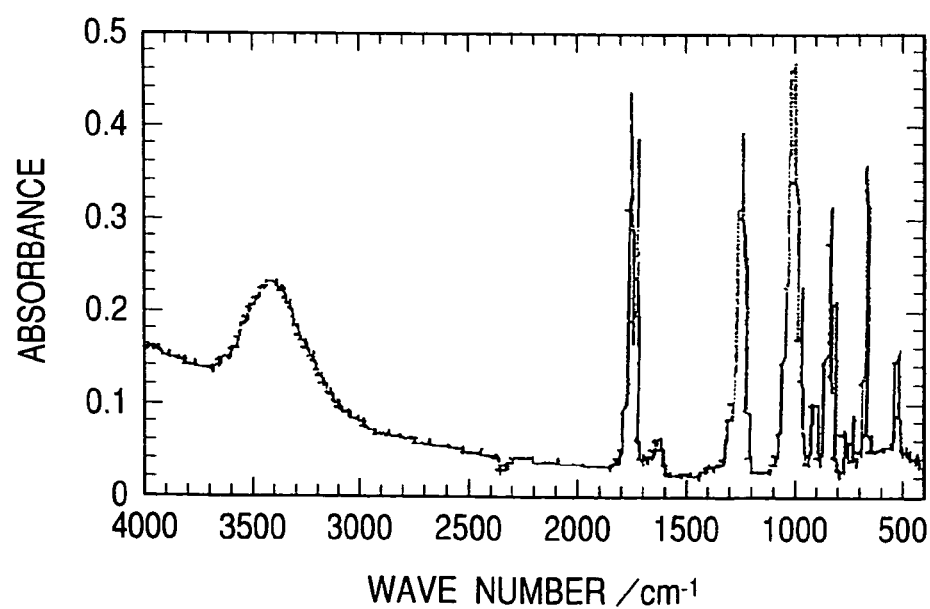
FIG. 3 is an infrared absorption spectral diagram showing yet another embodiment of the present invention.

After 6.7 g of boric acid, 18.3 g of lithium trichloroacetate, and 130 ml of dimethyl carbonate were put into a 300-ml three-neck flask, 100 g of trichloroacetate anhydride has been added dripwise while the entire mixture was being stirred under an ice-cooled status. After the dripping operation, the mixture has been stirred for about 10 more hours at 110 degrees C. Next, the solvent has been removed from the reaction agent and the thus-obtained solid has been heated under vacuum pressure to remove, by sublimating, the trichloroacetate included in the solid. After this, the sublimate has been recrystallized using tetrahydrofuran. The thus-obtained crystal has been vacuum-dried to obtain LB3 at a yield of 24%. An infrared absorption spectral diagram of the compound which has thus been obtained is shown as FIG. 3.

Infrared absorption: 1,770 cm$^{-1}$ (C=O), 1,040 cm$^{-1}$ (C—O). $^{11}$B-NMR spectrum (on a CD$_3$OD/trimethyl borate basis): δ-19.1 ppm. Ultimate analyses (Theoretical values in parentheses): Li=1.0(1.0)%, B=1.5(1.6)%, C=14.7(14.4)%. Melting point: 281° C.

(Embodiment 4)

The Synthesis and Identification of Lithium Tetrakis (Acetate) Borate (Hereinafter Referred to as LB4)

Figure 4:
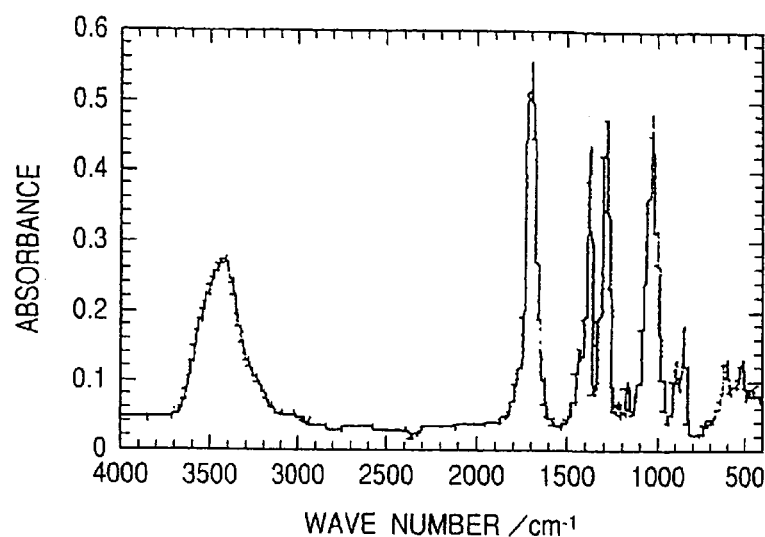
FIG. 4 is an infrared absorption spectral diagram showing a further embodiment of the present invention.

After 22.0 g of boric acid, 23.5 g of lithium acetate, and 327.0 g of acetic anhydride were put into a 500-ml three-neck flask, the mixture has been stirred for about 17 hours at 150 degrees C. Next, insoluble matter has been removed by filtering the reaction agent, and 760 ml of isopropyl alcohol has been added to the filtrate to achieve crystallization. The thus-obtained solid has been recrystallized using tetrahydrofuran, and LB4 has been obtained at a yield of 11%. An infrared absorption spectral diagram of the compound which has thus been obtained is shown as FIG. 4.

Infrared absorption: 1,700 cm$^{-1}$ (C=O), 1,040 cm$^{-1}$ (C—O). $^{11}$B-NMR spectrum (on a CD$_3$OD/trimethyl borate basis): δ-17.5 ppm. Ultimate analyses (Theoretical values in parentheses): Li=2.8(2.7)%, B=4.2(4.4)%, C=40.1(37.8)%, H=4.9(4.8)%. Melting point: 140° C.

(Embodiment 5)

The Synthesis and Identification of Lithium Tetrakis (Chlorodifluoroacetate) Borate (Hereinafter Referred to as LB5)

After 6.5 g of boric acid, 14 g of lithium chlorodifluoroacetate, and 100 ml of dimethyl carbonate were put into a 200-ml three-neck flask, 77 g of chlorodifluoroacetate anhydride has been added dripwise while the entire mixture was being stirred under an ice-cooled status. After the dripping operation, the mixture has been stirred for about 14 more hours at 80 degrees C. Next, the solvent has been removed from the reaction agent and the thus-obtained solid has been recrystallized using tetrahydrofuran. The thus-obtained crystal has been vacuum-dried to obtain LB5 at a yield of 45%.

$^{11}$B-NMR spectrum (on a CD$_3$OD/trimethyl borate basis): δ-18.0 ppm. Ultimate analyses (Theoretical values in parentheses): Li=1.3(1.3)%, B=1.8(2.0)%, C=18.1(17.9)%. Melting point: 150° C. (decomposition).

(Embodiment 6)

The Synthesis and Identification of Tetraethyl Ammonium Tetrakis (Trifluoroacetate) Borate (Hereinafter Referred to as AB1)

After 38.1 g of boric acid, 150 g of tetra ethyl ammonium trifluoroacetate, and 500 ml of dimethyl carbonate were put into a 1000-ml three-neck flask, 427 g of trifluoroacetate anhydride has been added dripwise while the entire mixture was being stirred under an ice-cooled status. After the dripping operation, the mixture has been stirred for about three more hours at 80 degrees C. Next, the solvent has been removed from the reaction agent and the thus-obtained solid has been recrystallized using tetrahydrofuran. The thus-obtained crystal has been vacuum-dried to obtain AB1 at a yield of 90%.

$^{11}$B-NMR spectrum (on a CD$_3$OD/trimethyl borate basis): δ-18.3 ppm. $^1$H-NMR spectrum (on a CD$_3$OD/TMS basis): δ-1.28 ppm (tt, CH$_3$, 12H), 3.28 ppm (q, CH$_2$, 8H). Ultimate analyses (Theoretical values in parentheses): B=1.9(1.8)%, C=32.5(32.4)%, H=3.4(3.4)%. N=2.4(2.4)%. Melting point: 124° C.

COMPARATIVE EXAMPLE 1, EMBODIMENTS 7 TO 11

Evaluating Solubility and Electroconductivity

Lithium bis-salicylate borate has been dissolved, as comparative example 1, in a substance (solvent A) that was created by mixing propylene carbonate (PC) and dimethyl carbonate (DMC) at a volume ratio of 1:2 as the solvent. As a result, the lithium bis-salicylate borate has been dissolved only to a concentration of 0.1 mol/dm$^{-3}$ (hereinafter, mol/dm$^{-3}$ is expressed as M). The electroconductivity of the nonaqueous electrolyte at this concentration has been 0.43 mS/cm when evaluated with the CM-60S conductivity meter (manufactured by Toh-A D.K.K.) that uses the CGT-511B cell.

In embodiment 7, lithium salt LB1 has been dissolved in solvent A. Consequently, LB1 has been dissolved to a concentration exceeding 1.2 M, and a maximum electroconductivity of 7.8 mS/cm has been obtained with 0.8 M. These results indicate that the use of lithium salt LB1 based on the present invention improves solubility and electroconductivity by factors of at least 12 and up to 18, respectively.

In embodiment 8, lithium salt LB2 has been dissolved in solvent A containing a 1:2 PC/DMC mixture. Consequently, LB2 has been dissolved to a concentration exceeding 1.2 M, and a maximum electroconductivity of 5.8 mS/cm has been obtained with 0.6 M. These results indicate that the use of lithium salt LB2 based on the present invention improves solubility and electroconductivity by factors of at least 12 and up to 13.4, respectively.

In embodiment 9, lithium salt LB3 has been dissolved insolvent A containing a 1:2 PC/DMC mixture. Consequently, LB3 has also been dissolved to a concentration exceeding 1.2 M, and a maximum electroconductivity of 4.3 mS/cm has been obtained with 0.5 M. These results indicate that the use of lithium salt LB3 based on the present invention improves solubility and electroconductivity by factors of at least 12 and up to 10, respectively.

In embodiment 10, lithium salt LB4 has been dissolved in solvent A containing a 1:2 PC/DMC mixture. Consequently, LB4 has been dissolved to a concentration exceeding 0.1 M, and an electroconductivity of 0.02 mS/cm has been obtained.

In embodiment 11, lithium salt LB5 has been dissolved in solvent A containing a 1:2 PC/DMC mixture. Consequently, LB5 has been dissolved to a concentration exceeding 1.2 M, and a maximum electroconductivity of 6.2 mS/cm has been obtained with 0.8 M. These results indicate that the use of lithium salt LB5 based on the present invention improves solubility and electroconductivity by factors of at least 12 and up to 14.4, respectively.

As described above, the bonds with the boron ions have been changed into oxygen-based single bonds to attain high solubility and electroconductivity by use of lithium salts based on the present invention.

COMPARATIVE EXAMPLES 2 TO 5, EMBODIMENTS 12 TO 14

Evaluating the Solubility Against a Fluorinated Solvent and Electroconductivity

Lithium bis-salicylate borate and lithium bis-benzenediolate have been dissolved, as comparative examples 2 and 3, respectively, by use of, as the noncombustible solvent, a substance (solvent B) that was created by mixing nonafluorobutyl methyl ether (tradename: HFE7100) and dimethyl carbonate (DMC) at the volume ratio of 80 versus 20 (HFE7100 versus DMC) where solvent B loses its flammability. As a result, in both comparative examples 2 and 3, a maximum solubility of 0.05 M has only been detected and no electroconductivity has been measurable.

Also, LiBF$_4$ and LiN (SO$_2$CF$_3$)$_2$ have been dissolved, as comparative examples 4 and 5, respectively, in solvent B. As a result, in comparative example 4, when LiBF$_4$ was dissolved to 0.1 M, the phase of the solvent has separated into two layers and no electroconductivity has been measurable. In comparative example 5, the corresponding compound has been dissolved to a concentration exceeding 1 M, and a maximum electroconductivity of 0.69 mS/cm has been obtained with a concentration of 1 M.

In addition, LB1, LB2, and LB5 have been dissolved, as embodiments 12, 13, and 14, respectively, in solvent B. As a result, in embodiment 11, LB1 has been dissolved to a concentration exceeding 1.2 M, and a maximum electroconductivity of 1.55 mS/cm has been obtained with a concentration of 0.8 M. That is to say, the use of LB1 has enabled electroconductivity to be improved by 2.2 times that of the comparative example 4 in which LiN (SO$_2$CF$_3$)$_2$ was used.

In embodiment 13, LB2 has also been dissolved to a concentration exceeding 1.2 M, and a maximum electroconductivity of 1.7 mS/cm has been obtained with a concentration of 0.6 M. That is to say, the use of LB2 has enabled electroconductivity to be improved by 2.4 times that of the comparative example 5 in which LiN $(SO_2CF_3)_2$ was used. In embodiment 14, LB5 has also been dissolved to a concentration exceeding 1.2 M, and a maximum electroconductivity of 1.8 mS/cm has been obtained with a concentration of 0.6 M. That is to say, the use of LB5 has enabled electroconductivity to be improved by 2.6 times that of the comparative example 5 in which LiN $(SO_2CF_3)_2$ was used.

It has been found that as described above, the organic lithium borate compounds pertaining to the present invention have high solubility against solvent mixtures heavily laden with a fluorinated solvent small in dipole moment and low in dielectric constant, and offer high electroconductivities at low concentrations in comparison to prior, well-known organic lithium borates. This means that the use of the organic lithium borate compounds pertaining to the present invention enables costs to be reduced by saving lithium salt consumption, and electrolytes of better characteristics to be obtained.

COMPARATIVE EXAMPLE 6, EMBODIMENTS 15 TO 18

Measurement of Aluminum Anodic Oxidation Currents

A nonaqueous electrolyte containing LiN $(SO_2CF_3)_2$ dissolved to a concentration of 0.7 M in solvent A has been prepared as comparative example 6. Likewise, a nonaqueous electrolyte containing LB1 dissolved to 0.7 M in solvent A, a nonaqueous electrolyte containing LB2 dissolved to 0.7 M in solvent A, a nonaqueous electrolyte containing LB3 dissolved to 0.7 M in solvent A, and a nonaqueous electrolyte containing LB5 dissolved to 0.7M in solvent A have been prepared as embodiments 15, 16, and 17, respectively. The anticorrosion performance of aluminum against anions has been evaluated using the above-mentioned electrolytes in order to perform the evaluations mentioned below. That is to say, a cell using aluminum as its working electrode and a lithium metal as its counter electrode and reference electrode, has been fabricated and evaluations have been performed on the current values obtained 10 minutes after the aluminum was maintained at a potential of 4.0 V (vs. the lithium metal).

As a result, a high current of 18 mA/cm$^2$ has been observed in comparative example 6. Also, the surface of the aluminum has changed to black after the above-mentioned test was continued for one hour. Conversely, the oxidation current values in embodiments 15, 16, and 17 have decreased to 10 μA/cm$^2$, 5 μA/cm$^2$, and 5 μA/cm$^2$, respectively, and the surface of the aluminum existing after the above-mentioned test was continued for one hour has suffered no visual changes in any sample.

It has been found that as described above, the use of the organic lithium borates pertaining to the present invention reduces, even at a high potential of 4 V, the anodic oxidation of aluminum to 1/1800 in embodiment 15 and 1/3600 in embodiments 16,17 and 18, respectively, in comparison to the LiN $(SO_2CF_3)_2$ in comparative example 6. This means that the use of the organic lithium borate compounds pertaining to the present invention enables the provision of highly soluble and highly electroconductive electrolytes suppressed in terms of aluminum current collector corrosion.

COMPARATIVE EXAMPLE 7, EMBODIMENTS 19 TO 22

Evaluation of Oxidation Decomposition Potential Values

Figure 5:
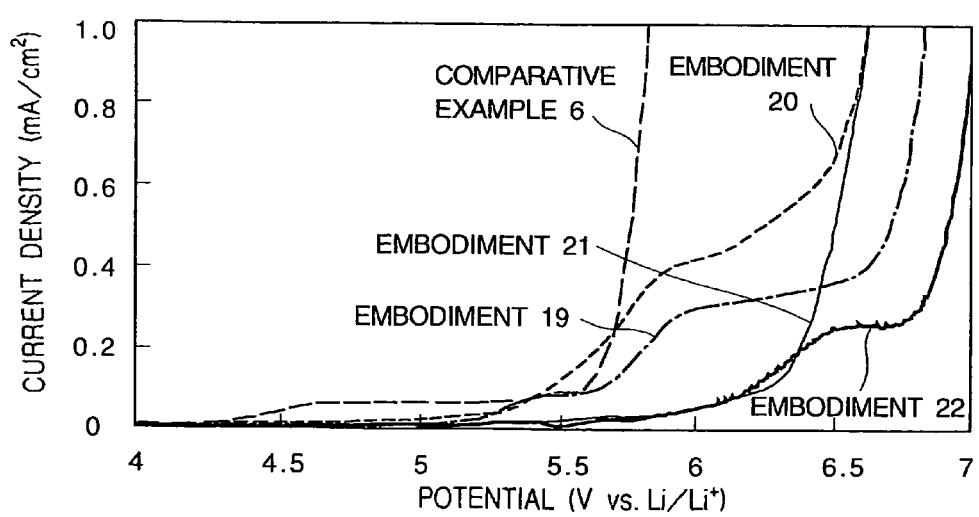
FIG. 5 is a cathode polarization curve.

A nonaqueous electrolyte containing LiN $(SO_2CF_3)_2$ that was dissolved to a concentration of 1 M, a nonaqueous electrolyte containing LB1 dissolved to 1 M, a nonaqueous electrolyte containing LB2 dissolved to 1 M, and a nonaqueous electrolyte containing LB3 dissolved to 1 M, and a nonaqueous electrolyte containing LB5 dissolved to 1 M have been prepared as comparative example 5 and embodiments 19, 20, 21 and 22, respectively, by use of PC as a highly acid-resistant solvent. By use of these nonaqueous electrolytes, the respective oxidation decomposition potential values have been compared using the method described below. That is to say, the oxidation currents against the potential values have been measured at a potential sweep rate of 10 mV/sec by application of an electrochemical cell using platinum as its working electrode and lithium as its counter electrode and reference electrode. Measurement results are shown in FIG. 5. For the LiN $(SO_2CF_3)_2$ in comparative example 7, significant changes in oxidation current from 5.8 V onward have been observed. Conversely to this, no significant changes in oxidation current have been observed until 6.7 V, 6.5 V, 6.4 V, and 6.8 V were reached in the cases of LB1 in embodiment 19, LB2 in embodiment 20, LB3 in embodiment 21, and LB5 in embodiment 22, respectively. In other words, oxidation resistance has improved at 0.9 V in LB1, 0.7 V in LB2, 0.6 V in LB3, and 1.0 V in LB5.

It has been found that as described above, the acetate displacement-type lithium salt of the present invention that uses boron as the central element of its anion is highly in solubility and in electroconductivity and does not corrode aluminum. It has also been found that the aforementioned lithium salt features a high oxidation potential and thus that the salt is a suitable material as the supporting electrolyte for a lithium battery high in capacity and in operating voltage.

COMPARATIVE EXAMPLE 87, EMBODIMENT 23

The Withstand Voltage Characteristics of Ammonium Salt

A nonaqueous electrolyte containing tetraethyl ammonium tetrafluoroborate $((CH_3CH_2)_4NFB_4)$ dissolved to a concentration of 1 M in PC has been prepared as example 8 for comparison. Similarly, a nonaqueous electrolyte containing-tetrakis (trifluoroacetate) borate $((CH_3CH_2)_4NB(OCO—CF_3)_4)$ dissolved to 1 M in PC has been prepared as embodiment 23. By use of these electrolytes, the corresponding potential windows have been evaluated at a sweep rate of 10 mV/sec by application of cyclic volumetry with an electrochemical cell using platinum as its working electrode and lithium as its counter electrode and reference electrode. As a result, potential values from 1.0 to 5.5 V have been obtained in comparative example 8, whereas those of embodiment 23 have been from 1 to 6 V and the potential window has therefore increased by 0.5 V at the oxidation side.

As can be seen from the above, even in the case of ammonium salt, the performance of a nonaqueous electrolyte can be improved by adopting anion structure based on the present invention. Since the capacity of an electric double-layer capacitor is proportional to the square of the withstand voltage characteristics V1 of the electrolyte, the use of the ammonium salt pertaining to the invention is expected to improve the capacity by about 1.2 times.

COMPARATIVE EXAMPLE 9

Figure 6:
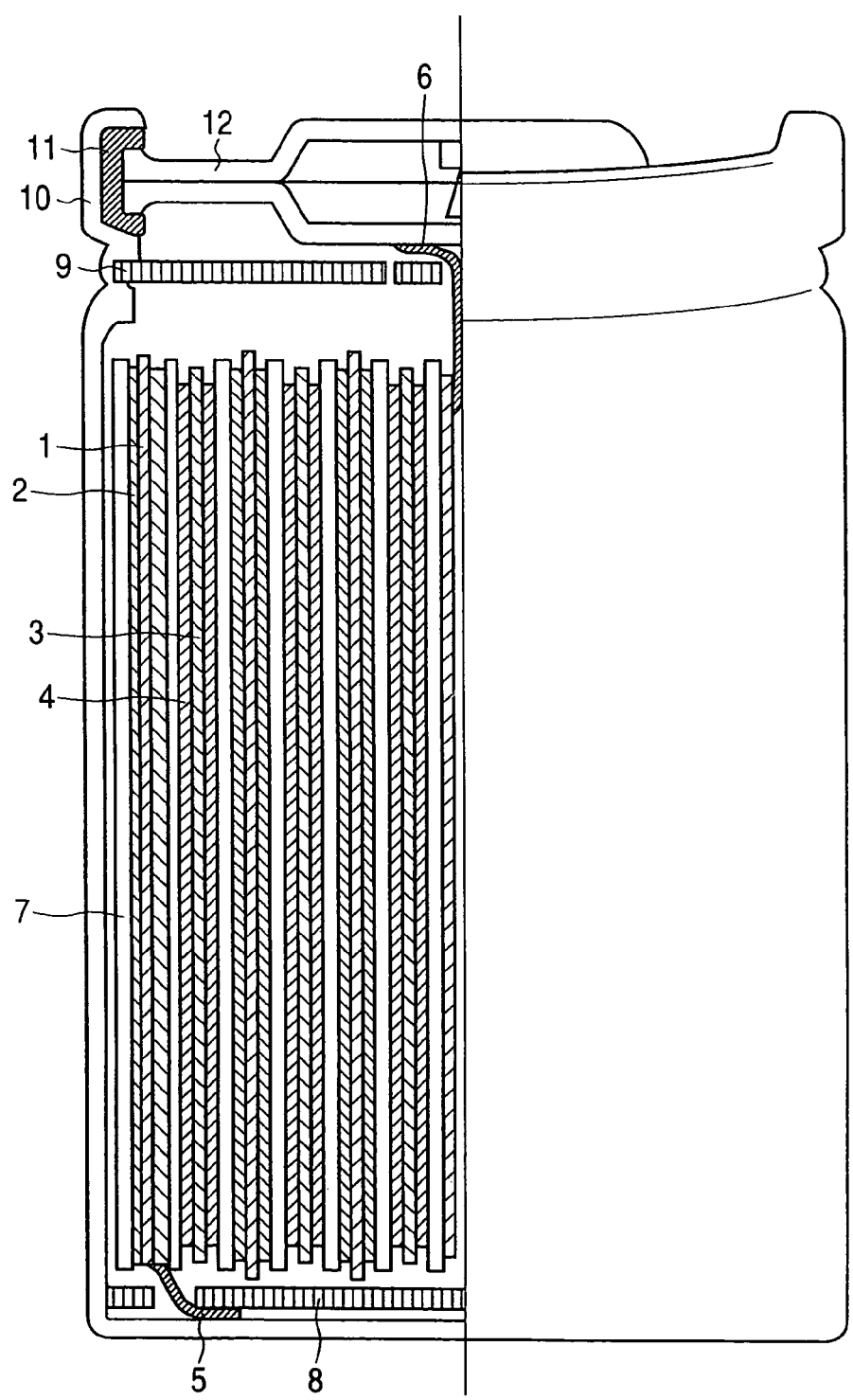
FIG. 6 is a cross-sectional view of a cylindrical battery, an embodiment of the present invention.

In order to conduct comparative evaluations on the high-temperature storage characteristics of a lithium secondary battery, a cylindrical lithium secondary battery of the structure shown in FIG. 6 has been fabricated using the method described below. Artificial graphite and PVDF have been used as a negative-electrode activation substance and a binding agent, respectively, then these substances have been mixed at a rate of 91:9 in terms of weight, and this mixture has been dissolved in N-methylpyrrolidone (hereinafter referred to as NMP), which is one type of solvent, and kneaded to obtain a negative-electrode paste material. Next, both sides of a copper foil used as a negative-electrode current collector 1 have been coated with the paste material, and then after the copper foil was dried, heated, pressurized, and vacuum-dried in that order, a negative electrode layer 2 has been formed on both sides of negative-electrode current collector 1 to obtain a negative electrode.

Cobalt acid lithium, graphite carbon, and PVDF have been used as a positive-electrode activation substance, a negative-electrode activation substance, and a binding agent, respectively, then these substances have been mixed at a rate of 85:7:8 in terms of weight, and this mixture has been dissolved in NMP, which is one type of solvent, and kneaded to obtain a positive-electrode paste material. Next, both sides of a copper foil used as positive-electrode current collector 3 have been coated with the paste material, and then after the copper foil was dried, heated, pressurized, and vacuum-dried in that order, a positive electrode layer 4 has been formed on both sides of positive-electrode current collector 3 to obtain a positive electrode.

After a negative electrode lead 5 and a positive electrode lead 6, both made of a nickel foil, were connected to uncoated portions of the negative electrode and positive electrode by electric welding, these electrodes have been placed among separators 7 and the outermost separator has been fixed by winding a tape around it to form an electrode group. Next after negative electrode lead 5 from this electrode group was routed through the bottom of a can and then inserted into an stainless-steel-made outer packaging can 10 via a polypropylene-made insulator 8 for electrical insulation, outer packaging can 10 and the other end of negative electrode lead 5 have been connected at the bottom of the can by electric welding to form a negative electrode circuit. The other end of positive electrode lead 6 has been connected to a positive electrode cap 12 via a positive-electrode insulator 9 by electric welding. An electrolyte has been prepared by dissolving 1M-concentration LiN $(SO_2CF_3)_2$ to 1 M $(mol/dm^{-3})$ in a solvent which was created by mixing ethylene carbonate (EC) and dimethyl carbonate (DMC) at a volume ratio of 1:2 (hereinafter, the composition of the electrolyte is shown as 1M-Lin $(SO_2CF_3)_2$ EC/DMC (1/2 in volume ratio)). After about 4 ml of the electrolyte was supplied from the hole in the previously fabricated battery negative-electrode outer packaging can 10, a cylindrical lithium secondary battery (cobalt-based battery) similar to that which was used in comparative example 1, has been fabricated by mechanically staking a positive electrode cap 12 equipped with a gasket 11, and negative-electrode outer packaging can 10.

After the current value and voltage value of this battery were set to 1 A and 4.2 V, respectively, the battery has been charged with the current and voltage values remaining fixed and under a charge-stopping current condition of 20 mA and then discharged at a current value of 1 A and a discharge-stopping voltage of 3 V. The discharge capacity at this time (hereinafter, this discharge capacity is referred to as the initial capacity of the battery) was 1,510 mAh. Next after the current value and voltage value of the battery were set to 1 A and 4.2 V, respectively, the battery has been charged with the current and voltage values remaining fixed and under a charge-stopping current condition of 20 mA. Furthermore, the battery has been left in its charged status for 20 days under an environment of 60 degrees C. After this, the battery has been removed from the test cell, then allowed to stand at room temperature for one day, and undergone temporary discharge to 3 V at a fixed current of 1 A, followed by fixed-voltage recharging at a fixed current of 1 A and under a stopping current condition of 20 mA. The discharge capacity obtained when the battery was discharged to 3 V at a fixed current of 1 A has been evaluated as an index of the battery storage characteristics (hereinafter, this index is referred to as the recovery capacity). The recovery capacity of this battery in comparative example 9 was 1,020 mAh. Accordingly, a value of 67% has been obtained as the maintenance ratio of the capacity with respect to the initial capacity of 1,510 mAh.

(Embodiment 24)

Similarly to comparative example 9, a battery has been fabricated as embodiment 24 by use of 1M-LB1 EC/DMC (1/2 in volume ratio) as its nonaqueous electrolyte. As a result of evaluation similar to that of comparative example 9, the initial capacity of this battery was 1,610 mAh. After high-temperature storage, the battery has attained a recovery capacity of 1,420 mAh, which was an increase of 400 mAh in comparison to the recovery capacity of the battery in comparative example 9. Also, the capacity maintenance ratio of the battery was 87%, which was 20% greater than in comparative example 9.

(Embodiment 25)

Similarly to comparative example 9, a battery has been fabricated as embodiment 25 by use of 1M-LB2 EC/DMC (1/2 in volume ratio) as its nonaqueous electrolyte. As a result of evaluation similar to that of comparative example 9, the initial capacity of this battery was 1,590 mAh. After high-temperature storage, the battery has attained a recovery capacity of 1,380 mAh, which was an increase of 360 mAh in comparison to the recovery capacity of the battery in comparative example 9. Also, the capacity maintenance ratio of the battery was 86%, which was 19% greater than in comparative example 9.

(Embodiment 26)

Similarly to comparative example 9, a battery has been fabricated as embodiment 26 by use of 1M-LB5 EC/DMC (1/2 in volume ratio) as its nonaqueous electrolyte. As a result of evaluation similar to that of comparative example 9, the initial capacity of this battery was 1,620 mAh. After high-temperature storage, the battery has attained a recovery capacity of 1,390 mAh, which was an increase of 370 mAh in comparison to the recovery capacity of the battery in comparative example 9. Also, the battery has attained a capacity maintenance ratio of 85%, which was 18% greater than in comparative example 9.

COMPARATIVE EXAMPLE 10

Similarly to comparative example 9, a battery has been fabricated as comparative example 10 by use of 1M-LiPF$_6$ EC/DMC (1/2 in volume ratio) as its electrolyte. The initial capacity of this battery was 1,650 mAh. Also, the recovery capacity and capacity maintenance ratio of the battery were 1,390 mAh and 85%, respectively.

(Embodiment 27)

An electrolyte for use in embodiment 27 has been prepared by dissolving 2-weight % LB1 in 1M-LiPF$_6$ EC/DMC (1/2 in volume ratio), and a battery has been fabricated as embodiment 27 by use of the above-mentioned electrolyte. The initial capacity of this battery was 1,640 mAh. After high-temperature storage, the battery has attained a recovery capacity of 1,430 mAh, which was an increase of 40 mAh in comparison to the recovery capacity of the battery in comparative example 10. Also, the battery has attained a capacity maintenance ratio of 87%, which was 2% greater than in comparative example 10.

(Embodiment 28)

An electrolyte for use in embodiment 28 has been prepared by dissolving 2-weight % LB2 in 1M-LiPF$_6$ EC/DMC (1/2 in volume ratio), and a battery has been fabricated as embodiment 28 by use of the above-mentioned electrolyte. The initial capacity of this battery was 1,630 mAh. After high-temperature storage, the battery has attained a recovery capacity of 1,410 mAh, which was an increase of 20 mAh in comparison to the recovery capacity of the battery in comparative example 10. Also, the battery has attained a capacity maintenance ratio of 86%, which was 1% greater than in comparative example 10.

(Embodiment 29)

An electrolyte for use in embodiment 29 has been prepared by dissolving 2-weight % LB5 in 1M-LiPF$_6$ EC/DMC (1/2 in volume ratio), and a battery has been fabricated as embodiment 29 by use of the above-mentioned electrolyte. The initial capacity of this battery was 1,660 mAh. After high-temperature storage, the battery has attained a recovery capacity of 1,450 mAh, which was an increase of 60 mAh in comparison to the recovery capacity of the battery in comparative example 10. Also, the battery has attained a capacity maintenance ratio of 87%, which was 2% greater than in comparative example 10.

(Embodiment 30)

An electrolyte for use in embodiment 30 has been prepared by dissolving 2-weight % LB1 and 2-weight % vinylene carbonate in 1M-LiPF$_6$EC/DMC (1/2 in volume ratio), and a battery has been fabricated as embodiment 30 by use of the above-mentioned electrolyte. The initial capacity of this battery was 1,640 mAh. After high-temperature storage, the battery has attained a recovery capacity of 1,460 mAh, which was an increase of 70 mAh in comparison to the recovery capacity of the battery in comparative example 10. Also, the battery has attained a capacity maintenance ratio of 89%, which was 4% greater than in comparative example 10.

COMPARATIVE EXAMPLE 11

Similarly to comparative example 98, a battery has been fabricated as comparative example 11 by use of 1M-LiN(SO$_2$CF$_3$)$_2$ HFE7100/DMC (8/2 in volume ratio) as its electrolyte. The initial capacity of this battery was 1,570 mAh. Also, the recovery capacity and capacity maintenance ratio of the battery were 1,110 mAh and 70%, respectively.

(Embodiment 31)

Similarly to comparative example 9, a battery has been fabricated as embodiment 31 by use of 1M-LB1 HFE7100/DMC (8/2 in volume ratio) as its nonaqueous electrolyte. The initial capacity of this battery was 1,610 mAh. Also, the recovery capacity and capacity maintenance ratio of the battery were 1,330 mAh and 82%, respectively, which were increases of 220 mAh and 12% in recovery capacity and capacity maintenance ratio, respectively, in comparison to the battery in comparative example 11.

(Embodiment 32)

Similarly to comparative example 9, a battery has been fabricated as embodiment 32 by use of 1M-LB2 HFE7100/DMC (8/2 in volume ratio) as its nonaqueous electrolyte. The initial capacity of this battery was 1,620 mAh. Also, the recovery capacity and capacity maintenance ratio of the battery were 1,350 mAh and 83%, respectively, which were increases of 240 mAh and 13% in recovery capacity and capacity maintenance ratio, respectively, in comparison to the battery in comparative example 11.

(Embodiment 33)

Similarly to comparative example 9, a battery has been fabricated as embodiment 33 by use of 1M-LB5 HFE7100/DMC (8/2 in volume ratio) as its nonaqueous electrolyte. The initial capacity of this battery was 1,630 mAh. Also, the recovery capacity and capacity maintenance ratio of the battery were 1,350 mAh and 82%, respectively, which were increases of 240 mAh and 12% in recovery capacity and capacity maintenance ratio, respectively, in comparison to the battery in comparative example 11.

As set forth above, the use of the organic lithium borate pertaining to the present invention greatly improves reliability with respect to high-temperature storage under a charged status. This is considered to be due to the fact that the improvement of oxidation resistance suppresses the acceleration of the anion with the decomposition temperature at high potential.

(Embodiment 34)

Figure 7:
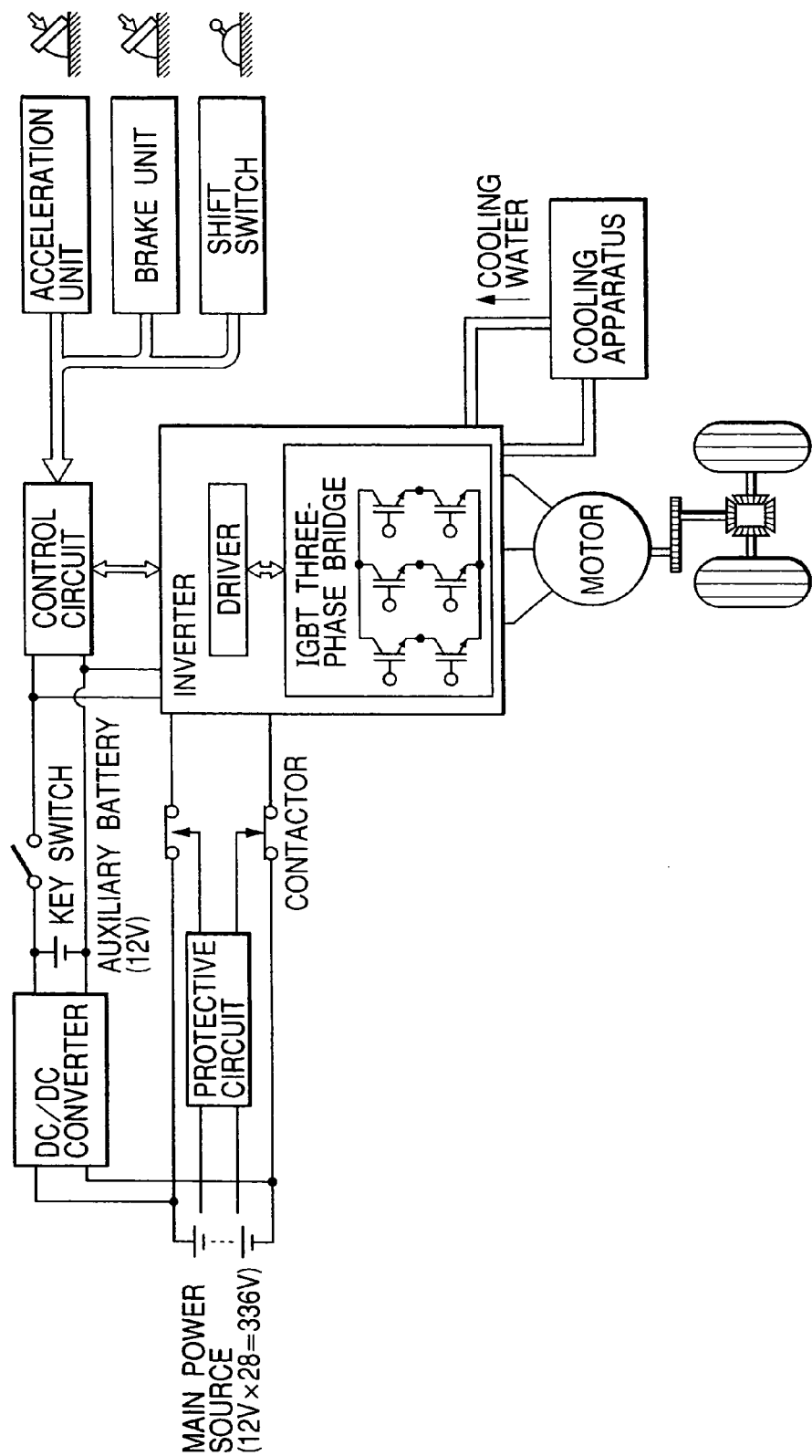
FIG. 7 is a block diagram showing the driving system of the electric automobile pertaining to the present invention.

FIG. 7 is a view showing the driving system configuration of an electric automobile which uses either of the lithium secondary batteries described in embodiments 24 to 33.

As with a normal type of gasoline vehicle, the electric automobile in FIG. 7 is constructed so that when the key switch is turned and the accelerator pedal is stepped, the torque or rotational speed of the motor inside will be controlled according to the particular stepping angle of the accelerator pedal. When the accelerator pedal is returned, a regenerative brake equivalent to an engine brake will be applied, and when the brake pedal is stepped, the regenerative brake force will further increase. Forward or reverse running of the vehicle is selected according to the particular status of the shift lever signal, and the transmission gear ratio is always kept constant. The vehicle employs an IGBT vector control inverter scheme using an induction motor, and a supply voltage of 336 V is determined from the IGBT withstand voltage. In this embodiment, the maximum output and maximum torque of the vehicle are set to 45 kW and 176 N.m, respectively, from its power performance (acceleration and climbing performance) as an automobile, and its rated output is set to 30 kW from the maximum speed specifications. The main control items include fail-safe control as well as forward and reverse running of the vehicle and regenerative control.

Since heat density increases with the dimensions and weight of the motor, it is important to adopt more efficient engine-cooling structure. Also, a general type of air cooling augments motor temperature increases. For these reasons, the engine in this embodiment employs water cooling, as with a general engine. The coolant circulation channel is provided in the aluminum frame shrouding the motor body, and thus the optimum configuration based on temperature rise simulation results is achieved. The coolant, after flowing in from the coolant inlet in the internal channel of the frame and absorbing the heat released from the motor body, is discharged and then cooled by a radiator provided in the coolant circulation channel. Such water-cooled structure has been adopted to improve cooling performance by about three times that of air cooling.

The inverter uses IGBT as its power device, and gives forth a maximum calorific value of several kilowatts during maximum output. Heat is also released from surge-absorbing resistors, filter capacitors, and more, and these components need to be controlled below a predetermined maximum allowable temperature in order to provide efficient cooling. It is particularly important to cool IGBT, and a method available to cool IGBT is either air cooling, water cooling, oil cooling, or others. In this embodiment, forced water cooling has been adopted because of its ease of handling and its high efficiency.

Figure 8:
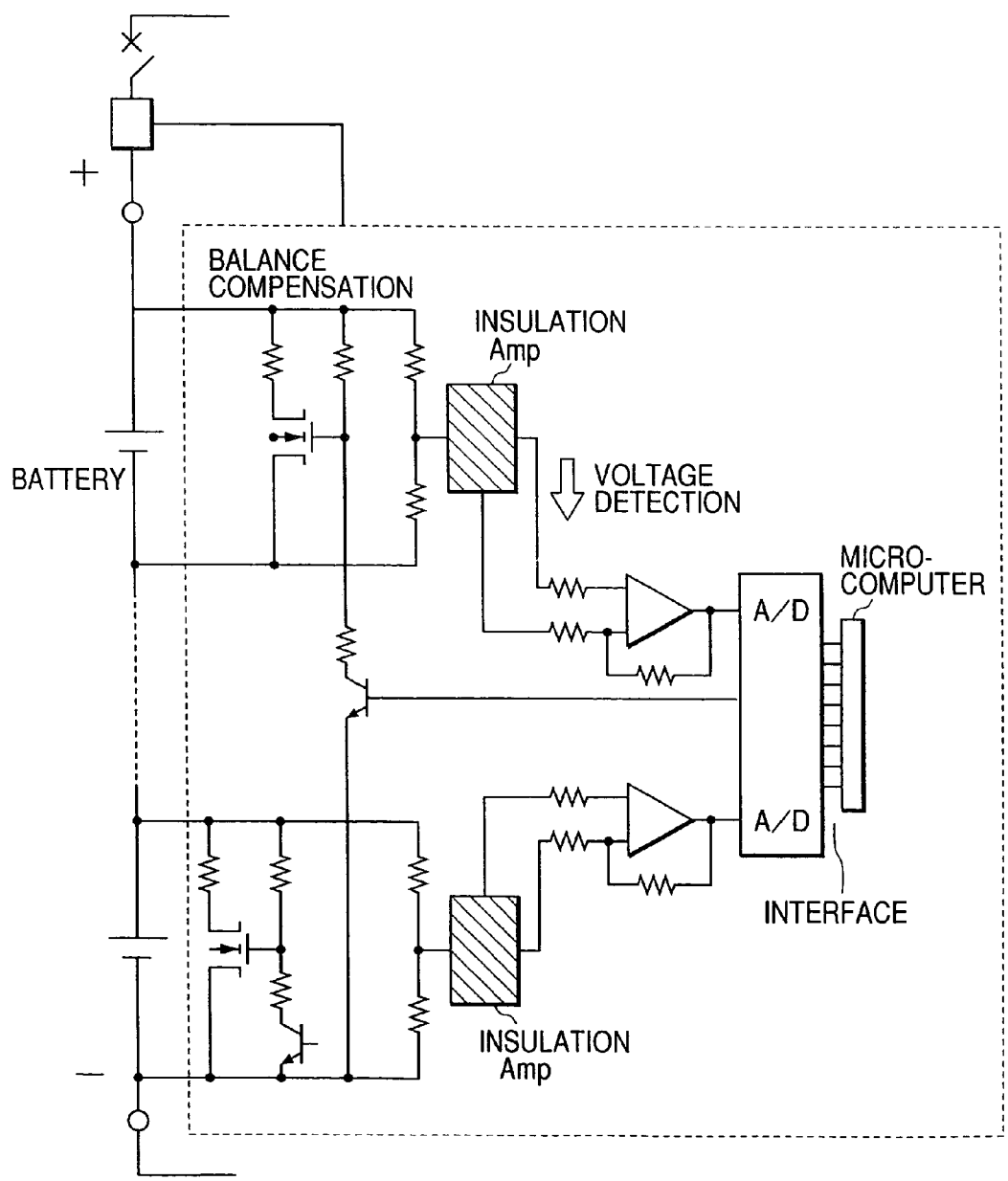
FIG. 8 is a protection circuit diagram relating to the present invention.

The protection circuit shown in FIG. 8 is formed in each lithium secondary battery used as the power supply in embodiments 31 to 33. This protection circuit protects the battery from overcharge and overdischarge. The protection circuit, as shown in FIG. 8, includes a balance-compensating circuit which adjusts the cell voltages of each battery, and is provided in each battery. This balance-compensating circuit is controlled by a microcomputer. Since conventional lithium secondary batteries use a flammable electrolyte, a thermistor is provided in each battery to detect and monitor temperature and pressure. In embodiments 31 to 33, however, nonflammable electrolytes not having a flashing point are used that do not require special temperature or pressure monitoring, since the electrolytes have the nature that even if a flame is brought into contact with the electrolyte, the flame will not ignite the battery fluid. Thereby, the number of safety devices required can be reduced by providing the protection circuit. As shown in FIG. 7, when overdischarge is detected, the power circuit will be automatically opened and closed.

Figure 9:
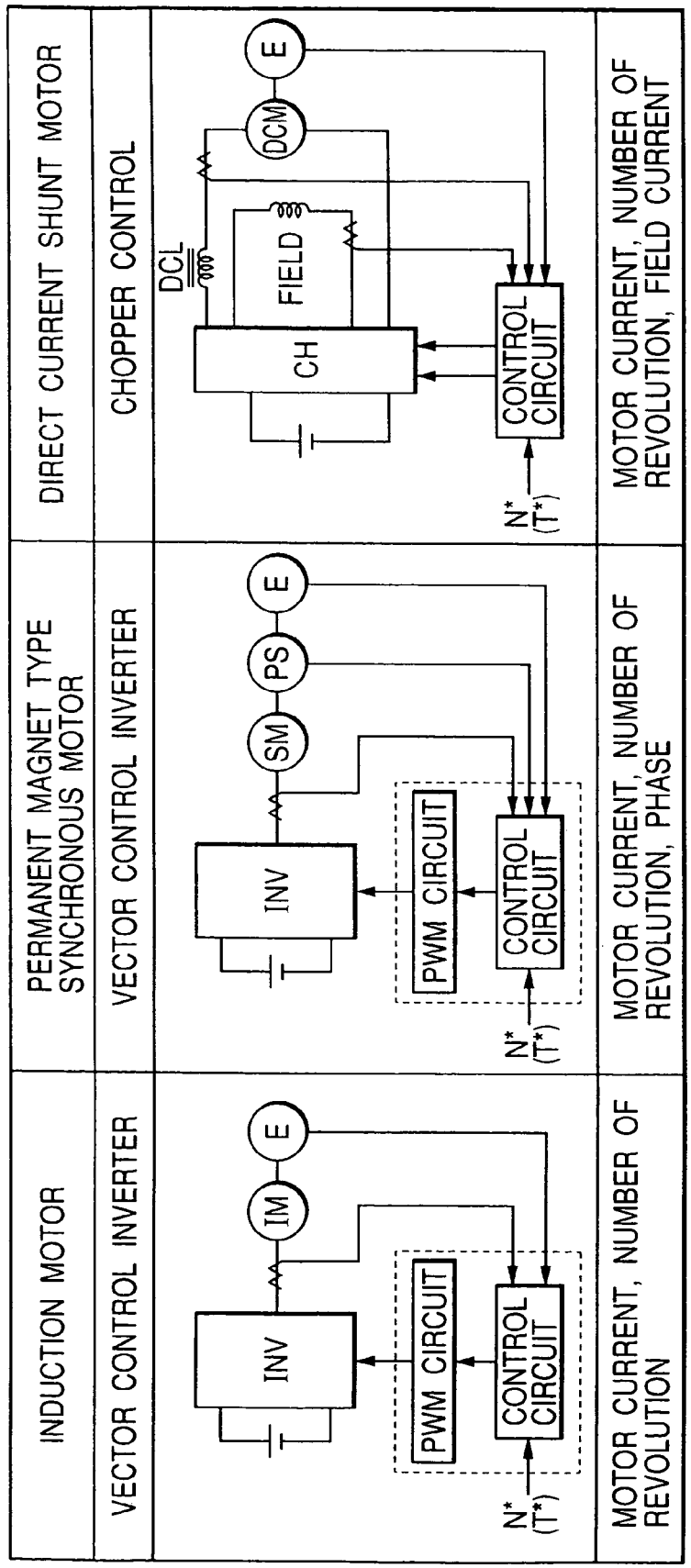
FIG. 9 is a block diagram showing the control system of the electric automobile pertaining to the present invention.

Although this embodiment shows an example in which an induction motor is used, this embodiment can likewise be applied to an electric automobile that uses, as shown in FIG. 9, a permanent magnet-type synchronous motor and a DC shunt motor. In the figure, INV stands for Inverter. Similarly, IM is short for Induction Motor, E for Encoder, SM for Synchronous Motor, PS for Position Sensor, PWM for Pulse Width Modulation, DCM for DC Motor, CH for Chopper, N* for speed command, and T* for torque command. Also, each line in the figure denotes a control motor type, a system configuration, and major control parameters.

(Embodiment 35)

Figure 10:
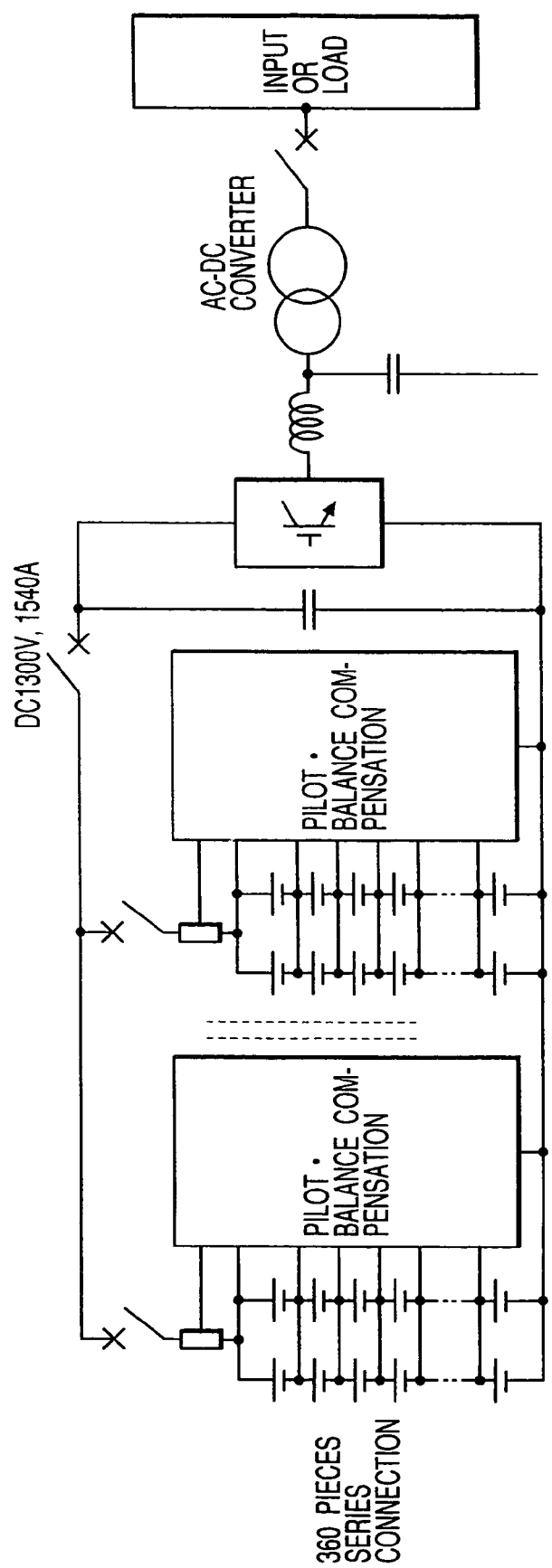
FIG. 10 is a block diagram showing the electric power storage system of the electric automobile pertaining to the present invention.

FIG. 10 is a block diagram showing a nighttime electric power storage system which uses a multitude of lithium secondary batteries described in either embodiment 30, 31, or 32. This example of an electric power storage system applies to a total battery capacity of 2,000 kW×4 h, a cell capacity of 1,000 Wh, series connection of 360 batteries, and parallel connection of 24 battery banks. As with embodiment 33, embodiment 35 also requires battery protection from overcharge and overdischarge and the protection circuit shown in FIG. 8 includes monitoring and balance-compensating circuits. In this embodiment, the batteries are protected similarly to embodiment 34.

Although intended for large-capacity electric power storage, this embodiment is also valid for a home-use air-conditioning system, an electric water heater, and the like.

What is claimed is:

1. An organic borate compound of formula (1)

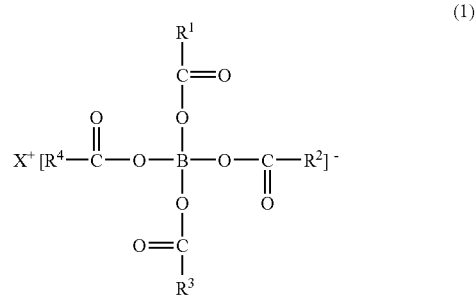

wherein X denotes lithium, and $R^1$, $R^2$, $R^3$, and $R^4$ each independently denotes a halogen-substituted alkyl group whose carbon number ranges from 1 to 4.

2. An organic borate compound as described in claim 1, wherein the groups denoted as $R^1$, $R^2$, $R^3$, and $R^4$ are trifluoromethyl or pentafluoroethyl.

* * * * *